US008470289B2

(12) United States Patent
Jaensch et al.

(10) Patent No.: US 8,470,289 B2
(45) Date of Patent: Jun. 25, 2013

(54) MANGANESE OXIDES AND THEIR USE IN THE OXIDATION OF ALKANES

(75) Inventors: Helge Jaensch, Houston, TX (US); Wilfried J. Mortier, Princeton, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 936 days.

(21) Appl. No.: 12/163,393

(22) Filed: Jun. 27, 2008

(65) Prior Publication Data
US 2009/0023972 A1  Jan. 22, 2009

Related U.S. Application Data

(60) Provisional application No. 60/949,997, filed on Jul. 16, 2007.

(51) Int. Cl.
*G01G 5/00* (2006.01)

(52) U.S. Cl.
USPC .............. 423/599; 423/275; 423/700; 423/50

(58) Field of Classification Search
USPC .................... 423/49–52, 21.5, 22, 54, 63, 70, 423/87, 112, 139, 275, 599, 700, 713
See application file for complete search history.

(56) References Cited

U.S. PATENT DOCUMENTS

| | | | |
|---|---|---|---|
| 3,214,236 A | 10/1965 | Weisz | |
| 5,183,945 A | 2/1993 | Stibrany et al. | |
| 5,198,580 A | 3/1993 | Bartek et al. | |
| 5,340,562 A | 8/1994 | O'Young et al. | |
| 5,523,509 A | 6/1996 | O'Young et al. | |
| 5,578,282 A | 11/1996 | O'Young et al. | |
| 5,597,944 A | 1/1997 | O'Young et al. | |
| 5,635,155 A | 6/1997 | O'Young et al. | |
| 5,695,618 A | 12/1997 | O'Young et al. | |
| 5,702,674 A | 12/1997 | O'Young et al. | |
| 5,772,898 A | 6/1998 | Lewis | |
| 5,922,920 A | 7/1999 | Bond et al. | |
| 6,486,357 B2 | 11/2002 | Suib et al. | |
| 6,503,476 B1 | 1/2003 | Suib et al. | |
| 6,646,158 B1 | 11/2003 | Khan et al. | |
| 6,720,462 B2 | 4/2004 | Kuhnle et al. | |
| 6,852,893 B2 | 2/2005 | Kuhnle et al. | |
| 7,985,883 B2 * | 7/2011 | Vartuli et al. | 568/376 |
| 2002/0128506 A1 | 9/2002 | Suib et al. | |
| 2003/0091499 A1 | 5/2003 | Becue et al. | |
| 2006/0019130 A1 | 1/2006 | Katikaneni et al. | |
| 2007/0196260 A1 * | 8/2007 | Kikkawa et al. | 423/409 |

FOREIGN PATENT DOCUMENTS

| | | |
|---|---|---|
| EP | 0010902 | 5/1980 |
| EP | 0608838 | 8/1994 |
| EP | 0710622 | 5/1996 |
| JP | 145249 | 6/1988 |
| JP | 1045643 | 2/1989 |
| JP | 3170445 | 9/1997 |
| WO | WO 2005/077498 | 8/2005 |
| WO | 2006/006531 | * 1/2006 |
| WO | WO 2006/015826 | 2/2006 |

OTHER PUBLICATIONS

Ai, M., "Oxidation of Propane to Acrylic Acid on V2O5-P2O5-Based Catalysts", Journal of Catalysis, 1986, vol. 101, pp. 389-395.
Chang, C.D. et al., "Manganese Nodules as Demetalation Catalysts", Ind. Eng. Chem. Process Des. Develop., 1974, vol. 13, pp. 315-316.
Giovanoli, R. et al., "A New Synthesis of Hollandite. A Possibility for Immobilization of Nuclear Waste", Chimia, 1981, vol. 35, No. 2, pp. 53-55.
Makwana, V.D. et al., "Selective oxidation of alcohols using octahedral molecular sieves: influence of synthesis method and property-activity relations", Catalysis Today, 2003, vol. 85, pp. 225-233.
Miyake, T. et al., "Synthesis of Al-containing octahedral molecular sieves and oxidation of cyclohexane with them", Applied Catalysis A: General, 2005, vol. 288, pp. 216-219.
Shen, Y.F. et al., "Manganese Oxide Octahedral Molecular Sieves: Preparation, Characterization, and Applications", Science, 1993, vol. 260, pp. 511-515.
Turner, S. et al., "Todorokites: A New Family of Naturally Occurring Manganese Oxides", Science, 1981, vol. 212, pp. 1024-1026.
Vetrivel, S. et al., "Co and Mn impregnated MCM-41: their applications to vapour phase oxidation of isopropylbenzene", Journal of Molecular Catalysis A: Chemical, 227, 2005, pp. 269-278.
Wang, J.Y. et al., "Cyclohexane functionalization catalyzed by octahedral molecular sieve (OMS-1) materials", Journal of Catalysis, 1998, vol. 176, pp. 275-284.
Wu, S.C. et al, "Use of Deep Sea Manganese Nodules as Catalysts for Reduction of Nitric Oxide with Ammonia", Atmospheric Environment, Pergamon Press, 1972, vol. 6, pp. 309-317.
Brock, S.L., et al., "A Review of Porous Manganese Oxide Materials", Chemical Material, 1998, vol. 10, pp. 2619-2628.
Ghosh, R., et al., "Liquid-phase epoxidation of olefins by manganese oxide octahedral molecular sieves", Journal of Catalysis, 2004, vol. 224, pp. 288-296.
Li, W-N., et al., "Synthesis of Single Crystal Manganese Oxide Octahedral Molecular Sieve (OMS) Nanostructures with Tunable Tunnels and Shapes", J. Phys. Chem. B, 2006 vol. 110, pp. 3066-3070.
Suib, S. "Microporous manganese oxides", Current Opinion in Solid State and Materials Science, 1998, vol. 3, pp. 63-70.
Wong, S-T., et al., "Synthesis and Characterization of Pillared Buserite", Inorganic Chemistry, vol. 31, No. 7, 1992, pp. 1165-1172.
"Phenol", Process Economics Report, Phenol Supp. B. No. 22, 1977, pp. 113-121, 261-263.
O'Young, C.L. et al., "Hydrothermal Synthesis of Manganese Oxides with Tunnel Structures," Synthesis of Microporous Materials, 1992, vol. 2, pp. 333-340.
Sheldon, R. et al., "Organocatalytic Oxidations Mediated by Nitroxyl Radicals", Adv. Synth. Catal., 2004, vol. 346, pp. 1051-1071.
Co-pending U.S. Appl. No. 60/950,008, filed Jul. 16, 2007.

* cited by examiner

*Primary Examiner* — Steven Bos
(74) *Attorney, Agent, or Firm* — Catherine L. Bell (57) ABSTRACT

Catalytic structures are provided comprising octahedral tunnel lattice manganese oxides ion-exchanged with metal cations or mixtures thereof. The structures are useful as catalysts for the oxidation of alkanes and may be prepared by treating layered manganese oxide under highly acidic conditions, optionally drying the treated product, and subjecting it to ion exchange.

21 Claims, 3 Drawing Sheets

MANGANESE OXIDES AND THEIR USE IN THE OXIDATION OF ALKANES

PRIORITY CLAIM

This invention clams priority to and the benefit of U.S. Ser. No. 60/949,997, filed Jul. 16, 2007.

FIELD OF THE INVENTION

The present invention is concerned with manganese oxide structures and their synthesis. Furthermore, the invention is particularly but not exclusively concerned with the oxidation of alkanes to produce oxygen-containing organic compounds. Such compounds may be alcohols, and carbonyl-containing compounds such as aldehydes, ketones and carboxylic acids. In particular the invention is concerned with the oxidation of $C_1$ to $C_5$ alkanes and more particularly methane, ethane and propane derived from natural gas.

BACKGROUND OF THE INVENTION

The availability of large quantities of natural gas has led to numerous proposals to upgrade the alkanes in the gas to more valuable chemicals including oxygen-containing organic compounds. The only commercial processes so far developed have required the sequential steps of catalytic dehydrogenation of the alkane to form an olefin followed by oxidation of the reactive olefinic site to produce the oxygenate. Other processes have been proposed for the direct oxidation of alkanes to oxygenates. However, these processes have low conversion and low selectivity and usually require high temperatures.

The two stage vapour phase oxidation of propylene to produce acrylic acid is known in the art. However, the production of acrylic acid from propane would be more attractive than its production from propylene because of the significant price difference between propane and propylene.

There are few references reported in the literature relating to the production of acrylic acid from propane. U.S. Pat. No. 5,198,580 (Standard Oil) discloses a process for partial oxidation of propane to yield acrylic acid, propylene, acrolein, acetic acid and carbon oxides. The process involves the reaction of propane in admixture with a molecular oxygen-containing gas in a reaction zone with a catalyst containing $Bi_b$, $Mo_c$, $V_v$, $A_a$, $D_d$, $E_e$, $O_x$; where A is one or more of K, Na, Li, Cs and Tl; D is one or more of Fe, Ni, Co, Zn, Ce and La; E is one or more of W, Nb, Sb, Sn, P, Cu, Pb, B, Mg, Ca and Sr; a, d and e is each from 0 to 10; b is from 0.1 to 10; c is from 0.1 to 20; v is from 0.1 to 10; c:b is from 2:1 to 30:1 and v:b is from 1.5:1 to 8:1. The acrylic acid yield achieved using the bismuth molybdate type of catalyst at a pressure of 138 kPag (20 psig) and a temperature of 400° C. is 5.4% at 19% conversion of propane.

EP-A-0608838 (Takashi et al/Mitsubishi) discloses a method of producing an unsaturated carboxylic acid, mostly in the explosive regime of the propane, air and water mixture, at 380° C. in the presence of a catalyst containing a mixed metal oxide of MoVTeXO, wherein X is at least one element selected from bismuth, cerium, indium, tantalum, niobium, aluminum, boron, tungsten, titanium, zirconium, chromium, manganese, iron, ruthenium, cobalt, rhodium, nickel, palladium, platinum and antimony. The proportion of the respective essential components is based on the total amount of the essential components exclusive of oxygen and satisfies the following formulae: $0.25 < r_{Mo} < 0.98$, $0.003 < r_V < 0.5$, $0.003 < r_{Te} < 0.05$, $0.003 < r_X < 0.5$, wherein $r_{Mo}$, $r_V$, $r_{Te}$ and $r_X$ are molar fractions of Mo, V, Te and X, respectively. Takashi et al also disclosed in Patent Number JP1045643 (9845643-February 1998), the formation of acrylic acid and acrolein in the presence of $P_aMo_bV_cW_dX_eO_n$ (X=Nb, Ta, Ti, Zr, Sb; if a=1 then b=1-18, c=0-4, d=0-4 and e=0.05-20) at 380° C. achieving a yield of 0.9% to acrolein and 3.5% to acrylic acid at 12% propane conversion U.S. Pat. No. 6,646,158 (SABIC) suggests the use of a catalyst with a calcined composition of $Mo_a$, $V_b$, $Ga_c$, $Pd_d$, $Nb_e$, $X_f$, wherein X=at least one element selected from the group consisting of La, Te, Ge, Zn, Si, In and W; a is 1; b is 0.01 to 0.9; c is >0 to 0.2; d is 0.000000001 to 0.2; e is >0 to 0.2; and f is >0 to 0.5, for the oxidation of propane to acrylic acid and acrolein. The numerical values of a, b, c, d, e and f represent the relative gram-atom ratios of the elements Mo, V, Ga, Pd, Nb and X respectively in the catalyst. The elements are preferably present in combination with oxygen in the form of various oxides.

The above referenced catalysts disclosed in the literature result in low yields of acrylic acid at relatively high temperatures and most produce propylene as one of the significant by-products. Propylene can be expensive to separate, especially in a recycling mode of operation.

Further examples are taught in the art for the mixed metal oxide component of catalysts for the production of acrylic acid in one step by subjecting propane to a vapour phase catalytic oxidation reaction. Such publications are a Mo—Sb—P—O type catalyst (EP-A-0010902 [Rohm and Haas]); a V—P—Te—O type catalyst (Journal of Catalysis, Col 101, p 389 (1986), a Bi—Mo—O type catalyst and a V—P—Te—O type catalyst (Japanese Unexamined Patent Publication No. 170445/1991). On the other hand, as an example of a catalyst for the production of methacrylic acid in one step by subjecting isobutene to a vapour phase catalytic oxidation reaction, a P—Mo—O type catalyst (Japanese Unexamined Patent Publication No. 145249/1988) is known.

However, each of the methods using such catalysts has a drawback, for example that the yield of the desired unsaturated carboxylic acid is not adequate or the reaction system is complex.

We have now developed a process that enables alkanes to be oxidised under less severe conditions and with a greater selectivity.

Manganese oxides having tunnel (4×4) structure are known and have been proposed as oxidation catalysts, for example in EP-A-0710622 (Texaco). An article in Catalysis Today 85 (2003) pages 225-233 describes the selective oxidation of alcohols using octahedral molecular sieves (OMS). These tunnel shaped manganese oxides contain significant quantities of lattice oxygen. It has been found that this lattice oxygen can be activated to provide available oxygen which can be used for oxidation of organic compounds such as benzyl alcohol to benzaldehyde, 2-butane and cyclohexane, as is described in Catalysis Today 85 (2003) pages 225-233.

It is also known, for example from U.S. Pat. No. 5,597,944 (Texaco) that a transition metal cation can be substituted in the framework of OMS-3 by co-dissolving a transition metal salt in the organic solvent used to dissolve the manganese salt. These materials are proposed as catalysts for the dehydrogenation of n-paraffins to n-olefins. The transition metal cation(s), which can be designated as M<+n> (where M indicates the transition metal and n indicates an oxidation state which is stable in the organic solvent solution), can be any metal selected from Groups IIIA, IVA, VA, VIA, VIIA, VIIIA, IB, IIB and VIIB of the Periodic Table of the Elements (Merck Catalogue of 2001 page 1287). Preferably, the transition metal is a metal selected from Groups IB, IIB and VIII of the Periodic Table of the Elements. Examples of useful framework-substituting transition metals are said to include Mg, Fe, Co, Ni, Cu, Ti, V, Cd, Mo, W, Cr, Zn, La, Ir, Rh, Pd and Pt. Preferred metals include Co, Cu, Ni, Zn, La and Pd. Transition metal cation(s) $M^{+n}$ should be present in the organic solvent in a concentration effective to introduce the desired proportions of the transition metal(s) into the framework of OMS-3 structure during the course of the reaction. Therefore, any suitable salt (inorganic or organic) of the selected transition metal(s) can be used which is sufficiently soluble provided, of course, that the anion does not interfere with the other reactants or the course of the reaction. For example, the nitrates, sulfates, perchlorates, alkoxides and acetates can be used with generally good results.

Manganese oxide octahedral molecular sieves possessing mono-directional tunnel structures constitute a family of molecular sieves wherein chains of MnO6 octahedra share edges to form tunnel structures of varying sizes. Such materials have been detected in samples of terrestrial origin and are also found in manganese nodules recovered from the ocean floor. Manganese nodules have been described as useful catalysts in the oxidation of carbon monoxide, methane and butane (U.S. Pat. No. 3,214,236 [Mobil]), in the reduction of nitric oxide with ammonia (Atmospheric Environment, Vol. 6, p. 309 (1972)) and in the demetallation of topped crude in the presence of hydrogen (Ind. Eng. Chem. Proc. Dev., Vol. 13, p. 315 (1974)).

The hollandites are naturally occurring hydrous manganese oxides with tunnel structures (also described as "framework hydrates") in which Mn can be present as $Mn^{+4}$ and other oxidation states. The tunnels can vary in size and configuration and various mono- or di-valent cations can be present in the tunnels. The hollandite structure consists of double chains of $MnO_6$ octahedra which share edges to form (2×2) tunnel structures. The average size of these tunnels is about 4.6 A° square. Ba, K, Na and Pb ions are present in the tunnels and coordinated to the oxygens of the double chains. The identity of the tunnel cations determines the mineral species. Specific hollandite species include hollandite (BaMn8O16), cryptomelane (KMn8O16), manjiroite (NaMn8O16) and coronadite (PbMn8O16). The hydrothermal method of synthesizing a manganese oxide octahedral molecular sieve possessing (2×2) tunnel structures such as those possessed by the naturally-occurring hollandites is described in "Hydrothermal Synthesis of Manganese Oxides with Tunnel Structures," in Synthesis of Microporous Materials, Vol. II, 333, M. L. Occelli, H. E. Robson Eds. Van Nostrand Reinhold, N.Y., 1992. Such synthetic octahedral molecular sieves having (2×2) tunnel structures are referred to in the art by the designation OMS-2.

The hydrothermal method of producing OMS-2 involves autoclaving an aqueous solution of manganese cation and permanganate anion under acidic conditions, i.e., pH<3, at temperatures ranging from about 80 to about 140° C. in the presence of counter cations having ionic diameters of between 2.3 and 4.6 A°. The counter cations can serve as templates for the formation of OMS-2 product and be retained in the tunnel structures thereof. Based on analytical tests, OMS-2 produced via this method is thermally stable up to 600° C. Alternatively, OMS-2 can be produced by the method disclosed in R. Giovanili and B. Balmer, Chimica, 35 (1981) 53. Thus, when manganese cation and permanganate anion are reacted under basic conditions, i.e., pH>12, a layered manganese oxide precursor is produced. This precursor is ion exchanged and then calcined at high temperatures, i.e., temperatures generally exceeding 600° C., to form OMS-2 product. Analytical tests indicate that OMS-2 produced via this method is thermally stable up to 800° C. and the average oxidation state of manganese ion is lower.

The todorokites are naturally occurring manganese oxides with (3×3) tunnel structures formed by triple chains of $MnO_6$ edge-sharing octahedra. Todorokites and related species are described by Turner et al. in "Todorokites: A New Family of Naturally Occurring Manganese Oxides", Science, Vol. 212, pp. 1024-1026 (1981). The authors speculate that since todorokites are often found in deep-sea manganese nodules containing high concentrations of copper and nickel, it is probable that such metals substitute for $Mn^{+2}$ in the octahedral framework.

Todorokites have attracted particular interest because of their relatively large tunnel dimension and their cation-exchange behaviour which is similar to that of zeolites (Shen et al., "Manganese Oxide Octahedral Molecular Sieves: Preparation, Characterization, and Applications", Science, Vol. 260, pp. 511-515 (1993)). The naturally occurring todorokites are poorly crystalline, impure in composition and coexist with other manganese oxide minerals. Results of high resolution transmission electron microscopy (HRTEM) show that todorokite contains random intergrowth material of 3×2, 3×3, 3×4 and 3×5 tunnel structure. Because of their disordered structure, the todorokites exhibit variable and non-reproducible catalytic activity, a drawback which militates against their commercial use.

A method of synthesizing a manganese oxide octahedral molecular sieve possessing (3×3) tunnel structures such as those possessed by the naturally-occurring todorokites is described in U.S. Pat. No. 5,340,562 (Texaco). Such synthetic octahedral molecular sieves having (3×3) tunnel structures are referred to in the art by the designation OMS-1.

OMS-1 can be prepared by reacting manganese cation and permanganate anion under strongly basic conditions to form a layered manganese oxide precursor; thereafter aging the precursor at room temperature for at least 8 hours; ion-exchanging the aged precursor; and then autoclaving the ion-exchanged precursor at from 150 to 180° C. for several days. Analytical tests indicate that OMS-1 produced via this method is thermally stable up to about 500° C.

We have now found that the framework of the 2×2 octahedral manganese compound may be ion-exchanged with metal cations to provide a new material and that this material may be used to oxidise alkanes. Our co-pending U.S. patent application Ser. No. 60/950,008, filed concurrently herewith discloses the use of manganese oxide molecular sieves as catalyst for the oxidation of alkyaromatic compounds to the corresponding hydroperoxides.

SUMMARY OF THE INVENTION

In accordance with one aspect of the present invention there is provided a 2×2 octahedral manganese oxide structure ion-exchanged with one or more metal cations.

In a second aspect of the present invention there is provided a method for producing a 2×2 octahedral manganese oxide structure containing metal cations, which process comprises treating a layered manganese oxide under highly acidic conditions comprising a pH not greater than 5, to rearrange the oxide to the 2×2 octahedral structure containing free protons, optionally drying the proton-containing structure, and ion exchanging the proton-containing structure with metal cations.

In a third aspect of the invention there is provided a process for the oxidation of an alkane comprising contacting the alkane with oxygen in the presence of a catalyst system comprising a 2×2 octahedral manganese oxide structure ion-exchanged with one or more metal cations.

DETAILED DESCRIPTION

We have found that the 2×2 structure is particularly stable and has benefits when ion-exchanged and used as a catalyst for the oxidation of alkanes. The alkanes are preferably C1 to C5 alkanes, and may be oxidised according to the invention as a single alkane or as a mixture of any two or more such alkanes. The alkane feed to oxidation may contain other components that do not substantially interfere with the target oxidation reaction.

In the oxidation process of the present invention the oxygen may be provided solely by the lattice oxygen of the manganese oxide. Alternatively additional oxygen such as molecular oxygen, as in air, may be provided.

In accordance with the present invention the octahedral porous manganese oxide molecular sieve possesses a (2×2) tunnel structure and contains cations of one or more metals as tunnel cations. The porous manganese oxide molecular sieve preferably complies with the general formula (I):

$$[A_{16-a}M_aMn_{16-a}O_{32}]_n \qquad (I)$$

in which
A represents a tunnel cation that may be in oxidation state +1, +2, +3, +4 or +5, wherein the metal of the cation is selected from the transition metals (Groups 3-12) and metals of Group 1 and Group 2 of the IUPAC Periodic Table of the Elements (1 Nov. 2004);
M represents a lattice cation that may be in oxidation state +1, +2, +3, +4 or +5, wherein the metal of the cation is a transition metal (Group 3-12);
Mn represents the transition metal, manganese;
a is a number equal to or greater than zero and less than 16; and
n is a number equal to or greater than 1.
Preferably, a is in the range of 0.1 to <16.

The porous manganese oxide may be hydrated, that is, it may have one or more $H_2O$ molecules associated with the general formula (I).

In the general formula (I), where there is more than one A then the A's may be the same or different with regard to oxidation state and/or metal.

Similarly, where general formula (I) has more than one lattice cation M, then the M's may be the same or different with regard to oxidation state and/or metal.

It will be recognized that A and M may be the same (transition) metal; but of course A is a tunnel cation whereas M is a lattice cation.

It will also be recognized that the lattice cation M and/or the tunnel cation A may be manganese.

Based on the preferred general formula (I), it will be recognized that the porous manganese oxide molecular sieves of the invention may be, for example, $K_{16}^{+1}Mn_{16}^{+3}O_{32}$, $K_8^{+1}Mn_8^{+3}Mn_8^{+4}O_{32}$, or $Mn_{16}^{+4}O_{32}$.

Many other combinations are possible depending on the values selected for a, the oxidation states of A, M and Mn, and the metals of A and M.

The octahedral manganese oxide molecular sieves of the invention possess an average pore diameter of approximately 4.6 Angstrom (Å). Preferably the manganese oxide octahedral molecular sieve possesses a highly uniform and homogeneous structure, i.e., one made up substantially entirely of (2×2) tunnel structure species without admixture of any significant amount of other tunnel structure species.

The metal cations in the manganese oxide structure of the invention are not necessarily homogenously dispersed throughout the structure. In one embodiment they may be more concentrated in certain zones or regions of the structure than others. Preferably the metal cations that have been ion-exchanged into the structure are more concentrated in surface zones or regions than elsewhere in the body of the oxide structure. It is believed to be beneficial for catalyst function to have such enrichment of the metal cations at or near the surfaces of the structure, and the ion exchange conditions employed may be adjusted to accomplish this configuration.

According to the second aspect of the invention there is provided a method for producing the 2×2 octahedral manganese oxide structure containing metal cations, as specified above. Preferably the highly acid conditions under which the layered manganese oxide is treated comprise a pH of 4 or less, more preferably 3 or less and most preferably 2 or less. For example the pH range for the treatment may be in the range 0.1 to 2, such as 0.5 to 1.5 or 0.1 to 1.1.

In one embodiment the method comprises mixing a solution of basic hydrogen peroxide and a solution of manganese nitrate hydrate at a basic pH to form the layered manganese oxide, treating the layered manganese oxide with acid to reduce the pH to the range of from 0.1 to 3 and to rearrange the layered oxide to form the octahedral 2×2 structure, drying, and treating the resulting octahedral 2×2 manganese oxide structure with a solution of metal ions to perform an ion exchange reaction with protons in the 2×2 octahedral structure.

Preferably the layered manganese oxide is formed from the mixture at a basic pH of from 11 to 14.

The metal cation-containing porous manganese oxide molecular sieves of the invention may be prepared by the method specified above. Generally stated, this method involves first producing the 2×2 tunnel octahedral molecular sieve (OMS-2) that does not contain tunnel metal cations; then introducing the tunnel metal cations.

A detailed description of a preferred embodiment of the synthesis method of the invention is provided hereinafter. Thus, a preferred synthesis of OMS-2 initially involves preparing a solution (I) of basic hydrogen peroxide; and a solution (II) of manganese nitrate hydrate. The hydrogen peroxide may be made basic for example by use of an alkali metal hydroxide such as KOH. Preferably the weight ratio KOH:$H_2O_2$ (35%):$H_2O$ is 1:3.5:31.5). In solution (II) the weight ratio $Mn(NO_3)_2*H_2O$:$H_2O$ is 1:11.4 [* indicates water of crystallisation; and the Mw of $Mn(NO_3)_2* H_2O=287.04$ g/mole]. The preferred synthesis involves mixing solution (I) and solution (II) by slowly adding solution (I) to solution (II). The reaction is preferably performed at a basic pH eg from 11 to 14. The mixed solutions are mixed, eg by stirring, for some time, preferably for 1 to 10 hours and preferably at room temperature. Then the reaction products are separated, eg centrifuged, in order to remove the solids. The solids are dried, such as by heating eg to 110° C. in an air-ventilated oven for eg 3 hours, and allowed to stand (material A). After grinding to a suitable particle size the dry material is calcined, eg for 6 hours at 500° C. in dry air (material B). Material B, which is a layered manganese oxide, is then treated under highly acidic conditions. Thus, it may be treated with diluted acid, preferably nitric acid, to reduce the pH to 5 or below, preferably 2 or below. Preferably the weight ratio $HNO_3$ [65%]:$H_2O$ in the diluted nitric acid is 1:2. Typical treatment is for eg 24 hours at about eg 100° C. and autogeneous pressure. It is notable that during this treatment the proton content increases while the potassium content decreases. Solids are removed eg by centrifugation and the recovered material is preferably washed with water. The material rearranges in this reaction to produce the 2×2 structure which then is dried (to produce material C). Drying may be for example for 3 hours at 110° C.

The metal cation-containing compounds of the present invention maybe prepared by treating the octahedral 2×2 manganese oxide structure (material C), for example in an autoclave at elevated temperature under autogeneous pressure, for a suitable time with a solution of the metal with which it is to be ion exchanged. The metal is preferably a transition metal. The compound in solution is preferably a salt or complex of the metal. This is preferably a (mixed) metal oxide precursor. The weight ratio of the metal compound eg transition metal salt(s), and material C can for example range between 0.2 and 5, depending on the metal source. For certain materials the addition of an acidifying agent such as nitric acid may be desirable. Material C is then treated as a slurry in the metal ion solution to effect cation exchange. For example, the exchange may be at 200° C. for 24 hours under autogeneous pressure. Thereafter the solids are removed, for example via centrifugation, and dried, for example for 3 hours at 110° C., to remove substantially all residual water. For certain materials it can be advantageous to then calcine, for example for 300° C. and 24 hours, followed by repeated washing steps.

Prior to use the catalytic materials, ie the cation-containing 2×2 octahedral manganese oxide structure, may be calcined again in order to fully convert them into their oxide form. Preferably they are fully converted into the oxide form when used as a catalyst.

In one embodiment of the synthesis, the ion-exchanged structures of the invention are produced by simultaneous treatment of the layered manganese oxide (material B) with the acid, eg nitric acid, and the metal, eg metal salt, followed by drying and optionally by calcination(s).

The preferred cation or mixture of cations that is ion exchanged with the protons in the 2×2 octahedral structure of the compound of the present invention will depend upon the use to which the compound is to be put. When it is to be used for alkane oxidation it will depend upon the alkane to be oxidised and the product that is to be produced. However, any metal cations that are redox active, such as transition metal cations, may be used. Indeed, any of the cations used to prepare mixed metal oxide catalysts that hitherto have been proposed in the art for the oxidation of alkanes may be used. Examples of such metals include the catalytic system which preferably comprises a calcined composition of $MO_a$, $V_b$, $Ga_c$, $Pd_d$, $Nb_e$, $X_f$, wherein X=at least one element selected from the group consisting of La, Te, Ge, Zn, Si, In and W; a is 1; b is 0.01 to 0.9; c is >0 to 0.2; d is 0.0000001 to 0.2; e is >0 to 0.2; and f is >0 to 0.5.

According to one embodiment of the invention the metal component employed as the metal tunnel cation(s) is a mixed metal component. Preferably, such mixed metal cation comprises $Mo_a$, $V_b$, $Ga_c$, $Pd_d$, $Nb_e$, $X_f$, (as mentioned above), and $O_y$, wherein y is a number determined by the valence requirements of the other elements in the catalyst composition.

When used as a catalyst, the metal-cation porous manganese oxide structures of the invention can be used with or without a support. Suitable supports for the catalyst include alumina, silica, titania, zirconia, molecular sieves such as zeolites and other micro or nonporous materials and mixtures thereof.

The synthesis method of the invention includes the introduction of metal cations into the structure. Preferably in the ion exchange reaction to provide the cation component of the final structure, ie catalyst system, the cation is provided from a solution of soluble compounds (salts, complexes or other compounds) of the or each of the metals. The solution is preferably an aqueous system having a pH of 1 to 10 and more preferably a pH of 1 to 7. Ion exchange is preferably performed at a temperature of from about 30 to about 100° C.

Where the cation is a mixture of compounds containing the desired metal elements, the mixture may be prepared by dissolving sufficient quantities of soluble compounds and dispersing the insoluble compounds so as to provide the desired gram-atom ratios of the elements in the composition. The final composition is then prepared by removing the water and/or other solvent from the mixture of the compounds in the solution system. The dried catalyst is preferably calcined by heating, preferably to a temperature in the range of from about 250° C. to about 600° C. in air or oxygen for a period of time that is preferably from about one hour to about 16 hours to produce the desired porous manganese oxide catalyst composition.

Molybdenum is one metal that is preferred for use as the tunnel cation metal, and preferably the molybdenum is introduced into the solution in the form of ammonium salts such as ammonium paramolybdate, or as organic acid salt of molybdenum such as acetates, oxalates, and glycolates. Other partially water soluble molybdenum compounds which may be used include molybdenum oxides, molybdic acid and chlorides of molybdenum.

Vanadium is another preferred cation metal and preferably the vanadium is introduced into the solution in the form of ammonium decavanadate or as organic salts of vanadium such as acetates, oxalates and tartrates. Partially water soluble vanadium compounds such as vanadium oxides and sulphates of vanadium can also be used. To achieve a complete solubility a certain amount of oxalic or tartaric acid may be added.

When gallium is used as the or one of the cation metals, the gallium is preferably introduced in the form of salts of gallium such as oxide, chloride, nitrate and the like.

Similarly if palladium is the or one of the cation metals, the palladium is preferably introduced as a solution of salts of palladium such as acetates, chlorides, nitrates and the like.

Other metals may be introduced in the form of salts of oxides, acetates, chlorides, nitrates or the like.

When niobium is used as the or one of the cation metals, it is preferably used in the form of oxalates or hydrate oxides. Other sources of this metal in soluble form include compounds in which the metal is coordinated, bonded or complexed to a beta-diketone, carboxylic acid, an amine, an alcohol or an alkanolamine.

According to one preferred embodiment in which the cation metal component is a mixed metal oxide component containing vanadium and molybdenum, the compounds of the present invention are prepared by the following general procedure. Aqueous solutions of vanadium and molybdenum are prepared separately. The vanadium solution is mixed with the molybdenum solution at a specified temperature and pH. The remaining required components (including the manganese oxide) are slowly added to the combined solutions. After mixing, the resultant gel is dried to incipient wetness with continuous stirring.

After drying the resultant gel mixture (preferably at 120° C. for 16 hours), the resultant structure, which may be useful as a catalyst, is heated, preferably to about 350° C. at a rate of preferably 2 degrees C. per minute and calcined at this temperature, preferably in air for a time to produce the desired oxide composition, for example about 4 hours.

The preferred mixed metal oxide used as cation compound in the catalyst system of the present invention comprises Mo, V, Te, O and X wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium, and cerium as essential components. Among the above elements for X, niobium, tantalum, tungsten and titanium are preferred. Particularly preferred is niobium.

The preferred proportions of the components based on the total amount of the components exclusive of oxygen are preferably within the ranges defined by the following formulas; $0.25 < r_{Mo} < 0.98$; $0.003 < r_V < 0.5$; $0.003 < r_{Te} < 0.5$; $0.003 < r_X < 0.5$ wherein $r_{Mo}$, $r_V$, $r_{Te}$ and $r_X$ are molar fractions of Mo, V, Te and X, respectively based on the total amount of the essential components exclusive of oxygen. For example when the above mixed metal oxide is represented by the empirical formula $Mo_a V_b Te_c X(1)_d X(2)_e O_n$ wherein X(1) and X(2) represent elements belong to the above-defined elements X, the respective molar fractions will be represented by the following formulas: $r_{Mo}=a/(a+b+c+d+e)$; $r_V=b/(a+b+c+d+e)$; $r_{Te}=c/(a+b+c+d+e)$; $r_X=(d+e)/(a+b+c+d+e)$.

As such proportions, the ranges represented by the following formulas are particularly preferred among the above molar fractions: $0.35 < r_{Mo} < 0.87$; $0.045 < r_V < 0.37$; $0.020 < r_{Te} < 0.27$; $0.005 < r_X < 0.35$.

The mixed metal oxide can be provided by ion exchange according to the present invention by the following method illustrated in relation to a mixed metal oxide of the formula $Mo_a V_b Te_c Nb_x O_n$. An aqueous solution of telluric acid, an aqueous solution of ammonium niobium oxalate and a solution or slurry of ammonium paramolybdate are sequentially added to an aqueous solution containing a predetermined amount of ammonium metavanadate, so that the atomic ratio of the respective metal elements would be in the prescribed proportions. The mixture is then provided to the 2×2 octahedral manganese oxide structure to enable the ion exchange to take place.

The ion exchanged material may then be dried and optionally calcined usually at a temperature from 350° C. to 700° C., preferably from 400 to 650° C. Calcination is usually performed for a period of from 0.5 to 30 hours, preferably from 1 to 10 hours. The calcination treatment may be conducted in an oxygen-containing atmosphere. However, it is preferred to conduct the calcination treatment substantially in the absence of oxygen. Specifically the treatment is preferably carried out in an inert gas atmosphere of e.g. nitrogen, argon or helium, or in vacuo.

The starting materials for mixed metal oxides are not limited to those described above. For example, a wide range of materials including oxides such as $MoO_3$, $V_2O_5$, $V_2O_3$, $TeO_2$ and $Nb_2O_5$, halides or oxyhalides such as $MoCl_5$, $VCl_4$, $VOCl_3$ and $NbCl_5$, alkoxides such as $Mo(OC_2H_5)_5$, $Nb(OC_2H_5)_5$, $VO(OC_2H_5)_3$ and acetylacetone molybdenyl and organometallic compounds may be used.

Where the compounds of the present invention are used as catalysts for the oxidation of alkanes, oxygen may be provided as lattice oxygen derived from the octahedral manganese oxide. Oxygen may, however, also be provided as additional molecular oxygen. The alkanes, eg propane and/or butane, should be contacted with the oxygen under oxidation conditions and the conditions that are preferably used will depend upon the nature of the alkane and the nature of the catalyst system. For example, the conditions may be different depending on whether the oxygen is all lattice oxygen or if additional oxygen is to be provided.

The oxidation reaction may be performed in the gas phase or the liquid phase, which may be solution or slurry. Gas phase is however preferred. Whatever the phase that is employed, the use of the catalyst system according to this invention provides a degree of flexibility to enhance the production of the desired oxygen containing materials. Although the preferred oxidation conditions are specific to the alkane to be oxidised and the oxygen containing product to be produced, the oxidation is typically performed with additional molecular oxygen generally provided as air.

Typically the oxidation process of the invention is performed at a temperature in the range 150° C. to 650° C., more typically 250° C. to 600° C., preferably 300° C. to 550° C. and more preferably 350° C. to 525° C. It is preferable to perform the oxidation reaction at elevated pressures.

Where propane is the alkane raw material to be oxidised, the source of the propane may be, for example, a gas stream which contains at least three volume percent of propane or a mixture of propylene and propane. The gas stream may also contain some amounts of C2 or C4 alkanes, preferably less than thirty volume percent of each. The gas stream, whatever the alkane, may also contain one or more diluents such as nitrogen, argon, carbon dioxide or water in the form of steam.

In carrying out the process with propane as the raw material, the reaction mixture preferably contains, proportionally, for one mole of propane, 0.01 to 2.0 moles of additional molecular oxygen, eg either as pure oxygen or in the form of air, and zero to 4.0 moles of water in the form of steam.

Molecular oxygen sources for the oxidation include purified oxygen, air and oxygen-enriched air, depending on the economics of separation and the hydrocarbon conversion achieved. The oxygen may be mixed with the alkane feed. The molar ratio of alkane to oxygen varies with the desired conversion and the selectivity of the catalyst, but is typically in the range of 1:1-1000:1.

The oxygen concentration in the feed gas mixture can vary widely, for example it may comprise from 0.1 to 50% by weight or higher of the feed mixture, provided proper measures to avoid explosion problems are applied. Air is the preferred source of oxygen in the feed. The amount of oxygen present is preferably a stoichiometric amount, or lower, in relation to the hydrocarbons in the feed.

The reaction can also be effected in the presence of diluents such as argon, nitrogen or steam. The weight ratio of alkane, eg propane or butane, to diluents, when present, is preferably in the range of 1:5-5:1.

ater vapour or steam may be used as a reaction diluent and as a heat moderator for the reaction. It also can act as a desorption accelerator for the reaction product in the vapour phase oxidation reaction. Other gases may be used as reaction diluents or heat moderators, such as helium, nitrogen and carbon dioxide.

The gaseous components of the reaction mixture preferably include alkane, oxygen or oxygen and diluents and these components are preferably uniformly admixed prior to being introduced into the reaction zone. The components may be preheated, individually or after being admixed, prior to being introduced into the reaction zone, which preferably has a temperature of from about 150° C. to about 450° C.

The reaction zone for the oxidation process of the invention preferably has a pressure of from 1 to 50 bar, and more preferably from 1 to 30 bar. The temperature is typically from about 150° C. to about 650° C., more typically from 250° C. to 600° C., preferably from 300° C. to 550° C. and most preferably from 350° C. to 525° C. The contact time between the reaction mixture and the catalyst is preferably from about 0.01 second to 100 seconds, more preferably from 0.1 second to 10 seconds. The space hourly velocity is preferably from about 50 to about 50,000 $h^{-1}$, more preferably from 100 to 10,000 $h^{-1}$ and most preferably from 200 to 3,000 $h^{-1}$.

The contact time is defined as the ratio between the apparent volume of the catalyst bed and the volume of the gaseous reaction mixture feed passing through the catalyst bed under the given reaction conditions per unit of time.

The space velocity is calculated by determining the total reactor outlet gas equivalent in litres of the total effluent evolved over a period of one hour divided by the litres of catalyst in the reactor. This room temperature volume is converted to the volume at 0° C. at 1 bar pressure.

The reaction pressure may be initially provided by the feed of the gaseous reactant and diluent and after the reaction has commenced, may be maintained by the use of a suitable back pressure controller placed on the reactor outlet stream.

The process may be carried out in a single stage with all the oxygen and reactants being supplied as a single feed with non-reacted initial reactants preferably being recycled. However, multiple stage addition of oxygen or hydrocarbon to the reactor may be used and/or recycling of un-reacted gases with purge mode can be applied to improve the overall productivity and/or yield of the desired products. Alternatively the process may be carried out using a staged reaction such as previously described.

The liquid products of the reaction may be separated from the unreacted feed hydrocarbons by condensation or scrubbing, for example scrubbing with water or dilute acid. The catalyst systems may be used for oxidizing alkanes such as $C_1$-$C_5$ alkanes, preferably $C_2$-$C_4$ alkanes such as ethane and/or propane and/or butane. The process produces corresponding oxygenated products such as acetic, acrylic and methacrylic acids. When normal and/or iso $C_4$ and $C_5$ alkanes are oxidised, for example in the vapour phase with molecular oxygen, the product is the corresponding alpha-beta unsaturated carboxylic acid. The invention is particularly useful for the oxidation of propane to acrylic acid and acrolein.

This invention further relates to:
1. A method for producing a 2×2 octahedral manganese oxide structure containing metal cations, which process comprises treating a layered manganese oxide under highly acidic conditions comprising a pH not greater than 5, to rearrange the oxide to the 2×2 octahedral structure containing free protons, optionally drying the proton-containing structure, and ion exchanging the proton-containing structure with metal cations.
2. The method according to paragraph 1 where the highly acidic conditions comprise a pH in the range of from 0.1 to 3.
3. The method according to paragraph 1 or 2 comprising mixing a solution of basic hydrogen peroxide and a solution of manganese nitrate hydrate at a basic pH to form the layered manganese oxide, treating the layered manganese oxide with acid to reduce the pH to the range of from 0.1 to 3 and to rearrange the layered oxide to form the octahedral 2×2 structure, drying, and treating the resulting octahedral 2×2 manganese oxide structure with a solution of metal ions to perform an ion exchange reaction with protons in the 2×2 octahedral structure.
4. The method according to paragraph 3 wherein the basic pH comprises a pH in the range of from 11 to 14.
5. The method according to any of the preceding paragraphs in which the ion-exchanged product material is calcined to convert it fully into its oxide form.
6. The method according to any of the preceding paragraphs in which the metal cations are redox active.
7. The method according to paragraph 6 in which the metal cations are transition metal cations.
8. The method according to any of the preceding paragraphs in which the cations are provided from a solution of one or more soluble compounds of the or each of the metals.
9. The method according to any of the preceding paragraphs in which the ion exchange reaction is performed at a pH in the range of from 1 to 10.
10. The method according to paragraph 9 in which the ion exchange reaction is performed at a pH in the range of from 1 to 7.
11. The method according to any of the preceding paragraphs in which the ion exchange reaction is performed at a temperature of from 30 to 100° C.
12. The method according to any of the preceding paragraphs in which the metal of the metal cations is selected from molybdenum, vanadium, gallium and palladium
13. The method according to any of the preceding paragraphs in which the metal cations comprise, as essential components, a mixture of metals comprising Mo, V, Te and X wherein X is at least one element selected from the group consisting of niobium, tantalum, tungsten, titanium, aluminium, zirconium, chromium, manganese, iron, ruthenium, cobalt, rhodium, nickel, palladium, platinum, antimony, bismuth, boron, indium and cerium.
14. A process for the oxidation of an alkane comprising contacting the alkane with oxygen in the presence of a catalyst system comprising a 2×2 octahedral manganese oxide structure ion-exchanged with one or more metal cations.
15. The process according to paragraph 14 wherein the contacting is performed at a temperature in the range of from 250° C. to 600° C.
16. The process according to paragraph 15 wherein the temperature is in the range of from 300° C. to 550° C.
17. The process according to paragraph 14 wherein the contacting is performed at a pressure of from 1 to 50 bar, and/or a temperature of from 300° C. to 550° C., and/or a contact time between the reaction mixture and the catalyst of from 0.01 sec to 100 sec, and/or a space velocity of from 50 to 50,000 $h^{-1}$.
18. The process according to any of paragraphs 14 to 17 in which the alkane comprises ethane, propane or butane.
19. The process according to any of paragraphs 14 to 18 in which the oxygen is provided solely by the lattice oxygen of the manganese oxide.
20. The process according to any of paragraphs 14 to 18 in which oxygen is provided as molecular oxygen.
21. The process according to paragraph 20 in which the alkane is propane and the reaction mixture contains, per mole of propane, from 0.01 to 2.0 moles of additional molecular oxygen and from 0 to 4.0 moles of water in the form of steam.
22. The process according to any of paragraphs 14 to 21 in which the metal cation is a transition metal cation.
23. The process according to paragraph 22 in which the transition metal is vanadium or molybdenum.

24. The process according to any of paragraphs 14 to 23 in which the metal cations comprise mixed metal cations.
25. The process according to paragraph 24 in which the metal cation mixture comprises, as essential components, Mo, V, Te, and X wherein X is at least one element selected from the group consisting of niobium, tantalum, tungsten, titanium, aluminium, zirconium, chromium, manganese, iron, ruthenium, cobalt, rhodium, nickel, palladium, platinum, antimony, bismuth, boron, indium and cerium.
26. The process according to any of paragraphs 14 to 25 in which the catalyst system has been calcined.
27. The process according to any of paragraphs 14 to 26 in which the catalyst system comprises metal cations that are non-homogeneously ion-exchanged into the manganese oxide.
28. The process according to paragraph 27 wherein the metal cations are more concentrated in a surface zone of the manganese oxide than elsewhere in the structure.
29. A 2×2 octahedral manganese oxide structure ion-exchanged with one or more metal cations.
30. The structure according to paragraph 29 in which the metal cation is a transition metal cation.
31. The structure according to paragraph 30 in which the transition metal is vanadium or molybdenum.
32. The structure according to any of paragraphs 29 to 31 in which the metal cation component comprises a mixture of metal cations.
33. The structure according to paragraph 32 in which the metal cation component comprises, as essential components, Mo, V, Te, and X wherein X is at least one element selected from the group consisting of niobium, tantalum, tungsten, titanium, aluminium, zirconium, chromium, manganese, iron, ruthenium, cobalt, rhodium, nickel, palladium, platinum, antimony, bismuth, boron, indium and cerium.
34. The structure according to any of paragraphs 29 to 33 that has been calcined.
35. The structure according to any of paragraphs 29 to 34 wherein the ion exchanged metal cations are non-homogeneously distributed in the manganese oxide.
36. The structure according to paragraph 35 wherein the metal cations are more concentrated in a surface zone of the manganese oxide than elsewhere in the structure.
37. The structure according to any of paragraphs 29 to 36 that has the general formula:

$$[A_{16-a}M_aMn_{16-a}O_{32}]_n \quad (I)$$

in which
A represents a tunnel metal cation in oxidation state +1, +2, +3, +4 or +5, wherein the metal of the cation is selected from the transition metals (Groups 3-12) and metals of Group 1 and Group 2 of the IUPAC Periodic Table of the Elements (1 Nov. 2004);
M represents a lattice metal cation in oxidation state +1, +2, +3, +4 or +5, wherein the metal of the cation is a transition metal (Group 3-12);
Mn represents the transition metal, manganese;
a is a number equal to or greater than zero and less than 16; and
n is a number equal to or greater than 1.
38. The structure according to paragraph 37 that comprises $K_{16}^{+1}Mn_{16}^{+3}O_{32}$, $K_8^{-1}Mn_8^{+3}Mn_{8+4}O_{32}$, or $Mn_{16}^{+4}O_{32}$.

The invention is illustrated by reference to the following Examples and the attached illustrative Figures. The X-ray diffraction data referred to in the Examples and shown in the Figures were collected with a Scintag powder X-Ray Diffractometer, in a Bragg-Brentano configuration and equipped with a Peltier-cooled detector, using copper K-alpha radiation. The diffraction data were recorded in a continuous scan mode at 1.20 degrees of two-theta/min., where theta is the Bragg angle.

Example 1

Preparation of Layered Manganese Oxide

Figure 1:
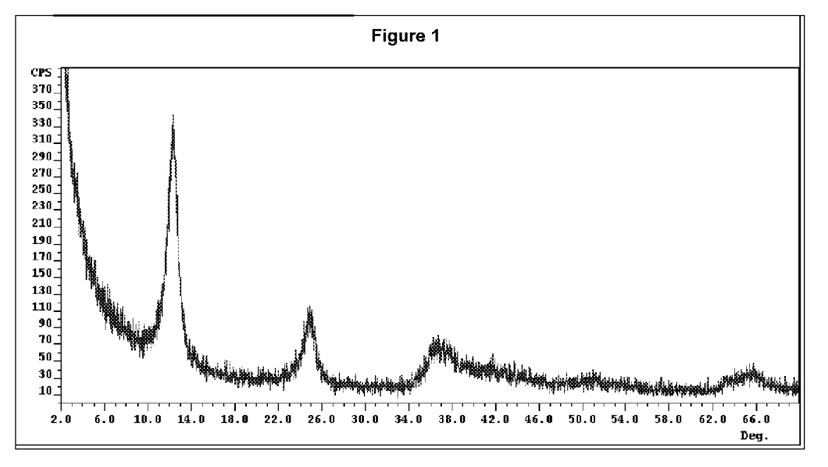
FIG. 1 is the X-ray diffraction (XRD) pattern of the layered manganese oxide material made in Example 1.

Layered $KMnO_2$ with birnessite structure was prepared by dropwise addition of 100 ml of a solution containing 2.86 g KOH (85%), 10 g aqueous $H_2O_2$ (35 wt %) and 90 g deionised water to 55 ml of a stirred solution containing 4.83 g $Mn(NO_3)_2$ hydrate (98%). The resulting slurry, which had a pH of about 14, was stirred for 2 h and then centrifuged at 4000 rpm for 10 min. After removing the clear supernatant liquid, the solids were dried at 110° C. for 3 h in an air-ventilated oven. The dried solids were then ground to a suitable size [approx. 0.250 mm mesh opening (60 mesh)] and calcined for 6 h at 500° C. in dry air. After cooling the solids were found by X-ray diffraction to have a layered structure as shown in FIG. 1.

Example 2

Rearrangement to 2×2 Octahedral Manganese Oxide Structure

Figure 2:
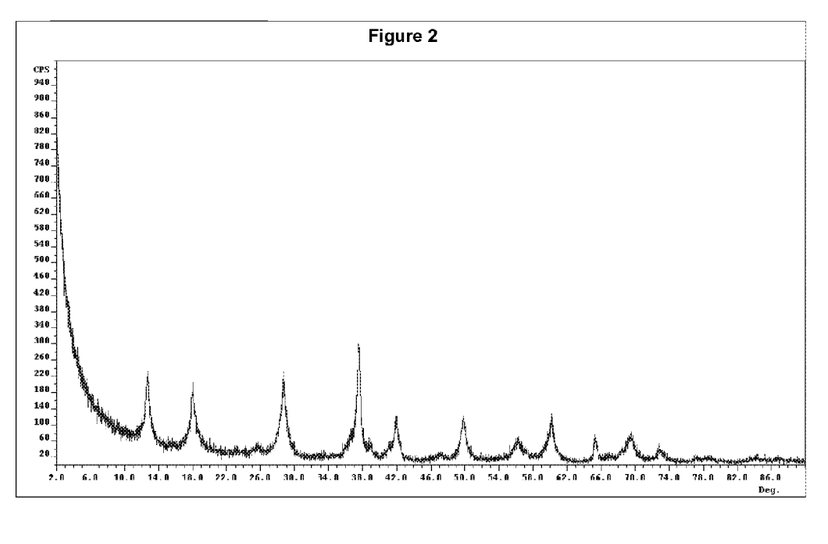
FIG. 2 is the XRD pattern of the proton-containing 2×2 octahedral manganese oxide material made in Example 2.

The layered $KMnO_2$ of Example 1 was treated with nitric acid, which caused a rearrangement to the cryptomelane 2×2 tunnel structure containing protons. The protons had been exchanged with the potassium ions by virtue of the highly acidic conditions, as evidenced by a pH of 1. The tunnel structure was confirmed by its X-ray diffraction pattern shown in FIG. 2. To accomplish the required rearrangement, 7.5 g of the layered $KMnO_2$ were added to a solution of 20.2 g of nitric acid (65%) and 40 g of water. The resulting suspension was placed in an autoclave and was then heated to 100° C. at autogeneous pressure for 24 hours. The resulting slurry (pH 1) was centrifuged for 30 min at 400 rpm. The clear supernatant was removed and the solids dried at 100° C. for 3 h in an air-ventilated oven. Alternatively the ion-exchanged solids were washed with 100 ml of deionised water, centrifuged again and dried as above.

Example 3

Ion Exchange with Transition Metal Cation

The proton-containing tunnel structure of Example 2 was ion exchanged with a solution of vanadyl sulphate. To effect this, 5 g of the H-exchanged tunnel type structure were combined with 50 g of water containing 1.0 g of $VOSO_4*3H_2O$. The resulting suspension was placed in an autoclave and heated to 200° C. for 24 hours at autogeneous pressure. The resulting slurry was centrifuged for 30 min at 400 rpm. The clear supernatant was removed and the solids dried at 100° C. for 3 h in an air-ventilated oven. The solids were verified as being vanadium cation exchanged 2×2 octahedral manganese oxide by means of energy dispersive X-ray spectroscopy (EDX).

Example 4

Simultaneous Rearrangement of Structure and Transition Metal Cation Exchange 3 g of the layered $KMnO_2$ of Example 1 were combined with 0.87 g of $VOSO_4*3H_2O$, 20 g of water and 10.1 g of nitric acid (65%). The resulting suspension was placed in an autoclave and heated to 200° C. for 24 h at autogeneous pressure. The resulting slurry was centrifuged for 30 min at 4000 rpm. The clear supernatant liquid (pH 1) was removed and the solids dried at 100° C. for 3 h in an air-ventilated oven. The solids were verified as being vanadium cation exchanged 2×2 octahedral manganese oxide by means of EDX.

Figure 3:
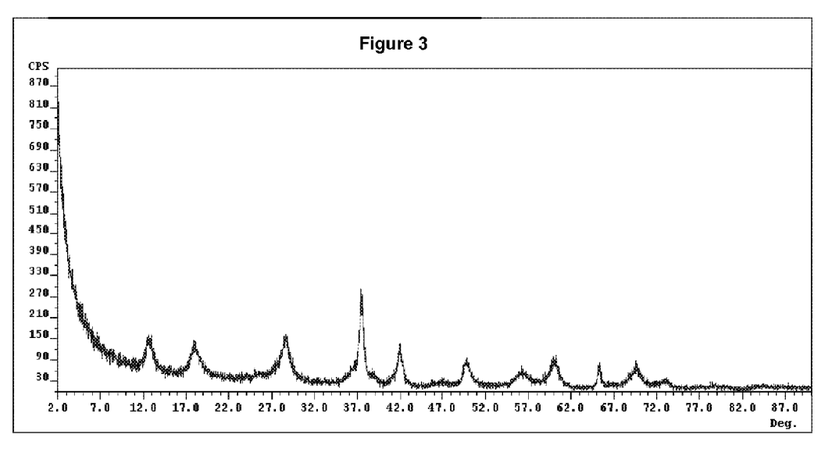
FIG. 3 is the XRD pattern of the vanadium cation exchanged 2×2 octahedral manganese oxide material made in Example 4.
Figure 4:
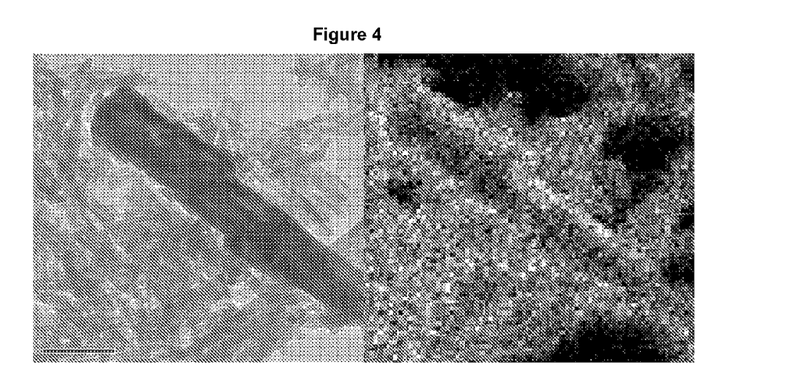
FIG. 4 is the Energy Dispersive X-ray spectrogram (vanadium-EDX) of the material made in Example 4.

The XRD pattern of this structure is shown in FIG. 3. Its morphology is shown in FIG. 4. The presence of vanadium ions close to the surface was verified by Energy Dispersive x-ray spectroscopy (EDX), the results of which are also shown in FIG. 4. From this it may be understood that the ion exchange is not necessarily homogeneous, but rather, this preparation resulted in a zoning of the vanadium cations. The areas of high vanadium content are indicated by the brightness of the spots in the EDX picture.

Example 5

Ion Exchange with Silver Cations

A silver exchanged 2×2 octahedral tunnel shaped manganese oxide was prepared by combining 5 g of the H-exchanged layered material prepared according to Example 2 with 1 g $AgNO_3$ and 50 g $H_2O$. The resulting suspension was placed in an autoclave and heated to 200° C. for 24 h at autogeneous pressure. The resulting slurry was centrifuged for 30 min at 4000 rpm. Then the clear supernatant liquid was removed and the solids dried at 100° C. for 3 h in an air-ventilated oven. The solids were silver cation exchanged 2×2 octahedral manganese oxide. The structure (2×2 tunnel) was verified by XRD.

Example 6

Oxidation of Butane

The vanadium cation exchanged 2×2 octahedral manganese oxide material produced in Example 4 was evaluated for effectiveness as a catalyst for butane oxidation. The material was pelletized and sieved to 300-500 nm catalyst particles. 3 g of these particles were loaded into a reactor, with the top and bottom of the reactor being filled with silicon carbide sand of similar particle size. The reactor was heated to 500° C. under flowing nitrogen. The high temperature nitrogen purge was to remove excess oxygen species adsorbed on the catalyst surface as well as oxygen traces left in the reactor. After purging, gaseous n-butane was introduced by syringe pump at reaction temperature. Performance was evaluated using both pulsed mode and continuous made introduction of the butane feed. In pulsed mode a sample of 10 ml butane was pumped at a flow rate of 50 ml/minute into a nitrogen stream flowing over the catalyst at 100 ml/minute, such that a plug of butane was pushed over the catalyst by the nitrogen. In continuous mode the flow of nitrogen to the reactor was out off and replaced with a continuous stream of butane only, at 100 ml/minute. Product samples were collected from the reactor by means of a heated rotating valve equipped with 16 sample loops in order to allow for adequate time resolution. The product samples were withdrawn from the reactor effluent in 5-10 sec intervals via the heated sampling valve, and analyzed by GC (gas chromatography).

The GC instrument and its method of use was as follows:
Detector: Thermal Conductivity Detector (TCD)
Column: CP-Poraplot Q-HT
Method: Start temperature=35° C. for 10 minutes
Heat up to 240° C. at 5° C./minute
Hold for 10 minutes at maximum temperature The evalution demonstrated that the vanadium cation exchanged 2×2 octahedral manganese oxide material catalysed the anaerobic gas phase oxidation of n-butane to n-butene and carbon dioxide, with the lattice oxygen appearing to be the source of oxygen (Mars-Van Krevelen conditions). The selectivity (%) to various products and conversion with time at 500° C. and a butane flow rate (pulsed and continuous mode) of 100 ml/minute butane is plotted in FIG. 5. This shows that a maximum selectivity of approximately 55% towards n-butene (the oxidative dehydrogenation product) at around 10% conversion was observed on the vanadium exchanged, porous manganese oxide catalyst. [Corresponding evaluations using as catalyst the H form porous manganese oxide prepared in Example 2, and a tellurium exchanged manganese oxide prepared in a manner similar to that used to produce the vanadium exchanged material, achieved approximately 30% selectivity towards n-butene]. In all cases carbon dioxide constituted the remaining oxidation product.

Figure 5:
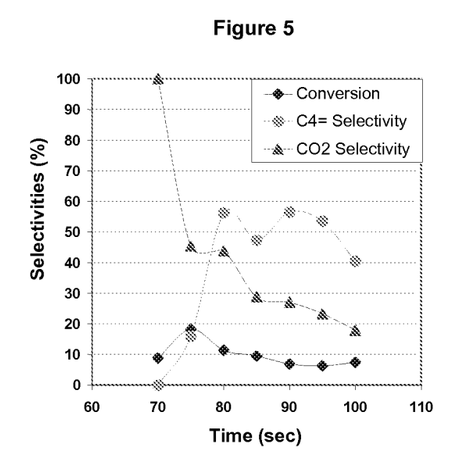
FIG. 5 is a plot of % selectivity versus time for the oxidation reaction described in Example 6.

As may be seen from FIG. 5, the initial activity of the catalyst is very high, converting the feed mainly to $CO_2$. With increasing time on stream the activity of the catalyst system decreases and the selectivity towards the dehydrogenation product n-butene increases at the expense of the total oxidation product $CO_2$. The observed increase in n-butene selectivity is consistent with lower oxidation potential due to the decrease in the average catalyst oxidation state (reduction of the catalyst) during the reaction.

After conducting the oxidation tests as described above, the vanadium containing porous manganese oxide catalyst that had been evaluated in pulsed mode was subjected to in situ regeneration with air oxygen (flow rate 100 ml/min) at elevated temperature (500° C.) for 1 hour and the pulsed mode oxidation test was rerun. The regeneration procedure was then repeated and the performance of the material under pulsed mode oxidation conditions was again determined. The results showed that for the same time on stream and under the same operating conditions, the activity of the catalyst decreases with the number of regenerations [12% conversion with fresh catalyst; falling to 8% and 7% after the first and second regenerations, respectively]. When the tests were carried out at similar conversions, the selectivity towards n-butene was found to increase [39% n-butene selectivity with fresh catalyst; rising to 46% and 48% after the first and second regenerations, respectively]. Thermogravimetric analysis (TGA) and temperature programmed oxidation (TPO) of the spent catalyst prior to regeneration indicated that there was no coke formation, which indicates that the activity decrease/selectivity increase is not due to active site moderation by coke.

While the present invention has been described and illustrated by reference to particular embodiments, those of ordinary skill in the art will appreciate that the invention lends itself to variations not necessarily illustrated herein. For this reason, then, reference should be made to the appended claims for purposes of determining the true scope of the present invention. All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. A method for producing a 2×2 octahedral manganese oxide molecular sieve structure containing metal cations, which process comprises mixing a solution of basic hydrogen peroxide and a solution of manganese nitrate hydrate at a basic pH to form a layered manganese oxide, treating the layered manganese oxide with acid to reduce the pH to the range of from 0.1 to 3 to rearrange the layered manganese oxide to the 2×2 octahedral structure containing free protons, optionally drying the proton-containing structure, and ion exchanging the proton-containing structure with metal cations to form an ion-exchanged product material, wherein the 2×2 octahedral manganese oxide molecular sieve structure is a tunnel structure.

2. The method according to claim 1 in which the ion-exchanged product material is calcined to convert the ion-exchanged product material fully into the ion-exchanged product material's oxide form.

3. The method according to claim 1 in which the metal cations are redox active.

4. The method according to claim 1 where the ion exchanging of the proton-containing structure with metal cations is performed at a pH in the range of from 1 to 10.

5. The method according to claim 1 in which the ion exchange reaction is performed at a temperature of from 30 to 100° C.

6. The method according to claim 1 in which the metal of the metal cations is selected from the group consisting of molybdenum, vanadium, gallium and palladium.

7. The method according to claim 1 in which the metal cations comprise, as essential components, a mixture of metals comprising Mo, V, Te and X wherein X is at least one element selected from the group consisting of niobium, tantalum, tungsten, titanium, aluminium, zirconium, chromium, manganese, iron, ruthenium, cobalt, rhodium, nickel, palladium, platinum, antimony, bismuth, boron, indium and cerium.

8. The method according to claim 1 in which the pH is reduced to a pH of 2 or less.

9. The method according to claim 1 in which the pH is reduced to a pH of 0.1 to 2.

10. The method according to claim 1 in which the pH is reduced to a pH of 0.5 to 1.5.

11. The method according to claim 1 in which the pH is reduced to a pH of 0.1 to 1.1.

12. A 2×2 octahedral manganese oxide structure ion-exchanged with one or more metal cations in which the metal cation component comprises, as essential components, Mo, V, Te, and X wherein X is at least one element selected from the group consisting of niobium, tantalum, tungsten, titanium, aluminium, zirconium, chromium, manganese, iron, ruthenium, cobalt, rhodium, nickel, palladium, platinum, antimony, bismuth, boron, indium and cerium.

13. The structure of claim 12 that has been calcined.

14. The structure of claim 12 wherein the ion exchanged metal cations are non-homogeneously distributed in the manganese oxide.

15. The structure according to claim 12 wherein the metal cations are more concentrated in a surface zone of the manganese oxide than elsewhere in the structure.

16. A porous manganese oxide molecular sieve, having a 2×2 tunnel structure, and having the general formula:

$$[A_{16-a}M_a Mn_{16-a} O_{32}]_n \quad (I)$$

in which:

A represents a tunnel metal cation in oxidation state +1, +2, +3, +4 or +5, wherein the metal of the cation is selected from the group consisting of transition metals (Groups 3-12) and metals of Group 1 and Group 2 of the IUPAC Periodic Table of the Elements (1 Nov. 2004);

M represents a lattice metal cation in oxidation state +1, +2, +3, +4 or +5, wherein the metal of the cation is a transition metal (Group 3-12);

Mn represents the transition metal, manganese;

a is a number equal to or greater than zero and less than 16; and n is a number equal to or greater than 1.

17. The structure according to claim 16 that comprises $K_{16}{}^{+1}Mn_{16}{}^{+3}O_{32}$, $K_8{}^{+1}Mn_8{}^{+3}Mn_8{}^{+4}O_{32}$, or $Mn_{16}{}^{+4}O_{32}$.

18. The structure of claim 16 wherein the tunnel metal cations are non-homogeneously distributed in the manganese oxide.

19. The structure according to claim 16 wherein the tunnel metal cations are more concentrated in a surface zone of the manganese oxide than elsewhere in the structure.

20. A method for producing a 2×2 octahedral manganese oxide structure containing metal cations, which process comprises treating a layered manganese oxide under highly acidic conditions comprising a pH not greater than 5, to rearrange the layered manganese oxide to the 2×2 octahedral structure containing free protons, optionally drying the proton-containing structure, and ion exchanging the proton-containing structure with metal cations to form an ion-exchanged product material, wherein the 2×2 octahedral manganese oxide structure is a tunnel structure, in which the metal cations are Mo, V, Te, and X wherein X is at least one element selected from the group consisting of niobium, tantalum, tungsten, titanium, aluminium, zirconium, chromium, manganese, iron, ruthenium, cobalt, rhodium, nickel, palladium, platinum, antimony, bismuth, boron, indium, and cerium.

21. A method for producing a 2×2 octahedral manganese oxide molecular sieve structure containing metal cations, which process comprises treating a layered manganese oxide under highly acidic conditions comprising a pH not greater than 5, to rearrange the layered manganese oxide to the 2×2 octahedral structure containing free protons, optionally drying the proton-containing structure, and ion exchanging the proton-containing structure with metal cations to form an ion-exchanged product material, wherein the 2×2 octahedral manganese oxide molecular sieve structure is a tunnel structure, wherein the metal cations comprise, as essential components, a mixture of metals comprising Mo, V, Te and X wherein X is at least one element selected from the group consisting of niobium, tantalum, tungsten, titanium, aluminium, zirconium, chromium, manganese, iron, ruthenium, cobalt, rhodium, nickel, palladium, platinum, antimony, bismuth, boron, indium and cerium.

* * * * *

UNITED STATES PATENT AND TRADEMARK OFFICE
CERTIFICATE OF CORRECTION

| | | |
|---|---|---|
| PATENT NO. | : 8,470,289 B2 | Page 1 of 1 |
| APPLICATION NO. | : 12/163393 | |
| DATED | : June 25, 2013 | |
| INVENTOR(S) | : Jaensch et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1067 days.

Signed and Sealed this
Sixth Day of January, 2015

Michelle K. Lee
*Deputy Director of the United States Patent and Trademark Office*